US006156738A

United States Patent [19]
Bell et al.

[11] Patent Number: 6,156,738
[45] Date of Patent: Dec. 5, 2000

[54] DIABETIC SUPPLEMENT BAR

[76] Inventors: Stacey J. Bell, 56 Amherst Rd.; Robert C. Jones, 109 Cross St., both of Belmont, Mass. 02178; Bruce R. Bistrian, 229 Argilla Rd., Ipswich, Mass. 01938; R. Armour Forse, 50 Fisher Ave., Brookline, Mass. 02146

[21] Appl. No.: 09/241,004

[22] Filed: Feb. 1, 1999

Related U.S. Application Data

[63] Continuation-in-part of application No. 08/815,595, Mar. 12, 1997, Pat. No. 5,866,555, which is a continuation-in-part of application No. 08/631,584, Apr. 12, 1996, abandoned.

[51] Int. Cl.$^7$ .............................................. A61K 31/715
[52] U.S. Cl. ........................... 514/60; 514/866; 424/439; 424/441
[58] Field of Search ..................... 514/60, 866; 424/439, 424/441

[56] References Cited

U.S. PATENT DOCUMENTS

| | | | |
|---|---|---|---|
| 4,220,666 | 9/1980 | Fields | 426/62 |
| 4,496,606 | 1/1985 | Michnowski | 426/658 |
| 4,703,063 | 10/1987 | Blackburn et al. | 514/552 |
| 4,833,128 | 5/1989 | Solomon et al. | 514/23 |
| 4,921,877 | 5/1990 | Cashmero et al. | 514/866 |
| 5,169,662 | 12/1992 | Spicer | 126/449 |
| 5,187,154 | 2/1993 | Philips et al. | 514/12 |
| 5,292,723 | 3/1994 | Audry et al. | 514/58 |
| 5,360,614 | 11/1994 | Fox et al. | 424/439 |
| 5,389,395 | 2/1995 | Joseph et al. . | |
| 5,470,839 | 11/1995 | Laughlin et al. . | |
| 5,480,865 | 1/1996 | Kingham . | |
| 5,545,410 | 8/1996 | Fox et al. | 424/439 |
| 5,549,905 | 8/1996 | Mark et al. | 424/439 |
| 5,571,783 | 11/1996 | Montagne | 426/658 |
| 5,576,306 | 11/1996 | Dressman et al. | 514/57 |
| 5,605,893 | 2/1997 | Kaufman | 514/60 |
| 5,612,074 | 3/1997 | Leach | 426/74 |

FOREIGN PATENT DOCUMENTS

| | | |
|---|---|---|
| 0 127 287 | 12/1984 | European Pat. Off. . |
| 0 482 715 | 4/1992 | European Pat. Off. . |
| 0 768 043 | 4/1997 | European Pat. Off. . |
| WO 95/24906 | 9/1995 | WIPO . |
| WO 96/31129 | 10/1996 | WIPO . |
| WO 97/02050 | 1/1997 | WIPO . |
| WO 97/28700 | 8/1997 | WIPO . |

OTHER PUBLICATIONS

Behall, K.M. et al. "Effect of Starch Structure on Glucose and Insulin Responses in Adults", *Am. J. Clin. Nutr.*, 47:428–432 (1988).

Boneh, A. et al. "Raw Cornstarch as an Additional Therapy in Nesidioblastosis", *Am. J. Clin. Nutr.* 47:1001–1003 (1988).

Franz, M.J. "Nutritional Strategies for Diabetes Control", *RD Fall* 1995:3–6 (1995).

Kaufman, F.R. et al., "A Randomized Crossover, Blinded Trial of Uncooked Cornstarch to Diminish Nocturnal Hypoglycemia at Diabetes Camp", *J. Inv. Med.* 43 (Suppl. 1):188A (1995).

Lozano, R. et al., "Cornstarch ingested after Oral Glucose Loading: Effect on Glucose Concentration, Hormone Response, and Symptoms in Patients with Postprandial hypoglycemic Syndrome", *Am. J. Clin. Nutr.* 52:667–670 (1990).

Poters, A.L. and M.B. Davidson, "Protein and Fat Effects on Glucose Responses and Insulin Requirements in Subjects with Insulin–dependent Diabetes Mellitus", *Am. J. Clin. Nurt.* 58:555–560 (1993).

Simpson, R.W. et al., "Food physical factors have different metabolic Effects in Nondiabetics and Diabetics", *Am J. Clin. Nutr.* 42:464–469 (1985).

Ververs, M.T.C. et al., "Complex Carbohydrates in the Prevention of Nocturnal Hypoglycemia in Diabetic Children", *Eur. J. Clin. Nutr.* 47:268–273 (1993).

Wolfsdorf, J.I. et al., "Optimal Daytime Feeding Regimen to Prevent Postprandial Hypoglycemia in Type 1 Glycogen Storage Disease", *Am. J. Clin. Nutr.* 56:587592 (1992).

Wolfsdorf, J.I. et al. "Physical Growth and Development of Children with Type 1 Glycogen–storage Disease: Comparison of the Effects of Long–Term use of Dextrose and Uncooked Cornstarch" *Am. J. Clin. Nutr.* 52:1051–1057 (1990).

Chen, Y. et al., "Cornstarch Therapy in type 1 Glycogen–Storage Disease," *New England Journal of Medicine* 310(3):171–175 (1984).

Crapo, P. et al., "Plasma Glucose and Insulin Responses to Orally Administered Simple and Complex Carbohydrates", *Diabetes*, 25:741–747 (1976).

Jenkins, D. et al., "The Glycaemic Response to Carbohydrate Foods", *The Lancot*, 2:388–391 (1984).

Parker, P.H. et al., "Nutritional Management of Glycogen Storage Disease", *Annu. Rev. Nutr.*, 13:83–109 (1993).

Smit, G.P.A. et al., "The Dietary Treatment of children with Type 1 Glycogen Storage Disease with Slow Release Carbohydrate", *Pediatric Research*, 18(9):879–881 (1984).

Wolfsdorf, J. et al., Continuous Glucose for Treatment of patients with Type 1 Glycogen–Storage Disease: Comparison of the Effects of Dextrose and Uncooked Cornstarch on Biochemical Variables[1–4] *Am. J. Clin Nutr,* 52:1043–1050 (1990).

*Primary Examiner*—James H. Reamer
*Attorney, Agent, or Firm*—Hamilton, Brook, Smith & Reynolds, P.C.

[57] ABSTRACT

A novel diabetic supplement bar which includes about 10–60% by weight simple carbohydrate, about 1–25% by weight protein, about 2–40% by weight lipid and about 1–60%, preferably about 5–35% by weight complex carbohydrate. This formulation is particularly useful for the treatment or prevention of nighttime hypoglycemia in diabetic patients who require insulin injections.

27 Claims, No Drawings

DIABETIC SUPPLEMENT BAR

RELATED APPLICATIONS

This application is a Continuation-in-Part application of application Ser. No. 08/815,595 now U.S. Pat. No. 5,866,555, filed Mar. 12, 1997, which is a Continuation-in-Part application of Ser. No. 08/631,584, filed Apr. 12, 1996 (now abandoned), the entire teachings of which are incorporated herein by reference.

BACKGROUND OF THE INVENTION

The present invention relates to the control of nighttime hypoglycemia in diabetics who require insulin injections. The invention utilizes a food bar which can be administered at bedtime to control blood glucose levels.

The results of a major study (Diabetes Control and Complication Trial)(Dawson, *Clinical Diabetes* 11:88–96, 1993), including over 1,400 diabetic patients who require regular insulin administrations, have indicated that patients who maintain blood sugar levels as close as possible to normal have fewer complications resulting in neuropathy, retinopathy, and kidney disease. To accomplish this result, many patients with diabetes today follow a strict regimen, known as the "tight control" regimen. This regimen requires that the patients closely monitor their blood sugar levels (e.g., multiple tests/day), judiciously use insulin in multiple doses, and strictly adhere to their diet. The unwanted side effect of tight glucose control is, however, that patients following this regimen have a three-fold increase in hypoglycemic events, more than half of which occur at nighttime.

Hypoglycemia is a dangerous condition which develops quickly and can cause neurologic damage as well as cause a patient to go into an unconscious state, and, in rare instances, a coma. Physicians want patients to be aware of the symptoms of hypoglycemia, e.g., coldness, shakiness, palpitations, and altered mentation, in order to avoid this condition. However, during sleep, the patients are not aware that they are developing hypoglycemia, so it is cricial to develop a treatment which can prevent this condition from developing at nighttime.

Today, patients with diabetes usually take a snack before they retire at night in attempt to avoid hypoglycemia in conjunction with a nighttime injection of insulin. The insulin is administered in order to keep the blood sugar level as close to normal as possible during sleep. Traditional snacks available today provide a carbohydrate source (usually sucrose and complex carboxydrates) which is released into the bloodstream after ingestion and is taken up by cells under the influence of insulin for use as energy or storage in the form of glycogen or fat. Because of the rapid release of some of these forms of carbohydrate into the bloodstream after the ingestion, some active insulin is left over in the body during the remainder of the night. This left over insulin has no more sources of carbohydrate to interact with due to a reduction in glucose release, thus resulting in nighttime hypoglycemia.

Thus, a need still exists for an improved bedtime snack which can provide a continual release of glucose during the nighttime into the bloodstream to interact with insulin, thereby maintaining normal glucose levels, and can prevent nighttime hypoglycemia in diabetic patients.

Accordingly, an object of the invention is to provide a novel diabetic supplement bar which allows constant bloodstream glucose level during the night, thus preventing nighttime hypoglycemia in a diabetic patient.

Another object of the invention is to provide a method of preventing or treating nighttime hypoglycemia in a diabetic patient by administering the diabetic supplement bar of the invention.

A further object of the invention is to control nighttime blood sugar levels of diabetic patients by administering the diabetic supplement bar of the invention near bedtime which provides phased release of glucose in the bloodstream.

These and other objects and features of the invention will be apparent from the following description and from the claims.

SUMMARY OF THE INVENTION

The present invention features a novel diabetic supplement bar which is used for a treatment or prevention of nighttime hypoglycemia in a diabetic patient. In preferred embodiments, the diabetic supplement bar provides 100 kcal nutrition per bar and has 1 "bread exchange" and ½ "fat exchange" as those terms have been defined by the American Diabetes Association.

The diabetic supplement bar includes about 10–60% by weight simple carbohydrate, more preferably the simple carbohydrate source provides about 4–55 kcal per 100 kcal. A simple carbohydrate source which provides about 40 kcal per 100 kcal is most preferred. The preferred simple carbohydrate is sucrose; the simple carbohydrate can also be glucose or dextrose.

The diabetic supplement bar further includes about 1–25% by weight protein, preferably about 10–20 kcal per 100 kcal, most preferably about 12 kcal per 100 kcal. In preferred embodiments, only the highest biological value proteins are used, e.g., whey, lactalbumin, casein, egg white, egg solids, soy and delactosed milk solid. Preferably, the protein source may be lactose-free.

The diabetic supplement bar further includes about 2–40% by weight lipid, preferably with the lipid source providing about 10–40 kcal per 100 kcal, most preferably about 27 kcal per 100 kcal. In preferred embodiments, the lipid source comprises a medium chain triglyceride and a long chain triglyceride, such as oils rich in gamma linolenic acid. The source of medium chain triglycerides is preferably coconut oil, palm oil, palm kernel oil, or mixtures thereof. The source of long chain triglycerides is preferably canola oil, safflower oil, sunflower oil, corn oil, olive oil, marine oils (e.g., menhaden oil), peanut oil, or mixtures thereof. In further preferred embodiments, the lipid source is provided in an amount sufficient to delay gastric emptying.

The diabetic supplement bar further includes about 1–60%, preferably about 5–35% by weight complex carbohydrate, preferably a complex carbohydrate source which provides about 10–35 kcal per 100 kcal, most preferably about 20 kcal per 100 kcal. The preferred complex carbohydrate is uncooked cornstarch. In other preferred embodiments, the complex carbohydrates can be selected from nuts, barley, bulgur, pasta, parboiled rice, dried legumes, or mixtures thereof.

In another aspect, the invention features the diabetic supplement bar which includes, in addition to the components described above (e.g., simple carbohydrates, proteins, lipids and complex carbohydrates) vitamins and minerals in accordance with, or approximately, the Recommended Dietary Allowance (RDA) (now called the Reference Daily Intake (RDI)).

The invention also features the diabetic supplement bar which includes, in addition to the components described above, inactive ingredients such as emulsifiers, artificial sweeteners and/or flavoring.

The invention also features, a method of treating or preventing nighttime hypoglycemia in a diabetic patient by administering a diabetic supplement bar to the patient, the diabetic supplement bar including about 10–60% by weight simple carbohydrate, about 1–25% by weight protein, about 2–40% by weight lipid and about 1–60%, preferably about 5–35% by weight complex carbohydrate.

In another aspect, the invention also features a method of controlling nighttime blood sugar levels in a diabetic patient by administering a diabetic supplement bar to the patient near bedtime, the diabetic supplement bar including about 10–60% by weight simple carbohydrate, about 1–25% by weight protein, about 2–40% by weight lipid and about 1–60%, preferably about 5–35% by weight complex carbohydrate.

The following description and non-limiting examples further elucidate the invention.

DETAILED DESCRIPTION OF THE INVENTION

The diabetic supplement bar of the invention is made by blending simple carbohydrates, proteins, lipids, complex carbohydrates, and any additional additives, and homogenizing the mixture into a food bar. The food bar can contain a variable number of calories, depending upon design choice and end-user.

Although not wishing to be bound by theory, it is believed that the diabetic supplement bar of the invention prevents or treats nighttime hypoglycemia by allowing carbohydrates to be released in three phases during the night, thus providing continual flow of glucose into the blood stream to interact with insulin. The three phases are as follows: (1) a fast release of carbohydrates from simple carbohydrates, e.g., sucrose, which is readily absorbed and enters the blood stream as glucose shortly after the ingestion of the bar; (2) a more slow release phase of carbohydrates into the bloodstream from protein used by the liver for gluconcogenesis. The protein gluconeogenesis allows a slow and even flow of glucose into the blood stream commencing after the glucose from the simple carbohydrate has been cleared; and (3) a slow release of simple carbohydrates from the hydrolysis of complex carbohydrates, e.g., corn starch. Complex carbohydrates are hydrolyzed by intestinal enzymes more slowly than other forms of carbohydrates, resulting in delayed intestinal absorption long after the bar is ingested. Lipids in the form of medium and long chain triglycerides are added to the bar both as an energy source and to delay overall gastric emptying, so that all of the aforementioned processes occur more slowly.

In practice of the present invention, sucrose is the preferred source of simple carbohydrates. While glucose and dextrose may also be used, fructose should be avoided as fructose has undesirable effects on the metabolism which include lactic acid production and impairment of gluconeogenesis by the liver.

The lipid source of the diabetic supplement bar of the invention may comprise medium chain triglycerides (MCTs), long chain triglycerides (LCTs), oils rich in gamma linolenic acid (GLA; e.g., evening primrose oil, borage oil), and combinations thereof Examples of suitable MCT sources include coconut oil, palm oil, palm kernel oil, or mixtures thereof. Examples of suitable LCT sources canola oil, safflower oil, sunflower oil, corn oil, olive oil, marine oils (e.g., menhaden oil), peanut oil, or mixtures thereof. The lipid source should be added to the diabetic supplement bar in the amount sufficient to delay gastric emptying. Additional sources of MCTs and LCTs are discussed in U.S. Pat. No. 4,703,062, which is herein incorporated by reference.

The protein may be any suitable protein utilized in a nutritional formula such as soy protein, casein protein, whey protein, animal and vegetable protein, and mixtures thereof. For greatest use, the protein source should be lactose-free so it can be used for lactose intolerant patients. When choosing a protein source, the biological value of the protein should be considered first, with the highest biological values being found in casein, whey, lactalbumin, egg albumin, and whole egg proteins. Next, the cost should be considered, the lowest cost with the best biological value being the best combination.

Uncooked cornstarch is the preferred source of complex carbohydrate because it carbohydrate content is relatively uniform, its rate of metabolism is both known and consistent, and it can be readily formulated into an easy to administer food bar. Additional sources of complex carbohydrates which can be used in the practice of the present invention include nuts, barley, bulgur, pasta, parboiled rice, dried legumes, or mixtures thereof. Uncooked cornstarch is commercially available from a number of suppliers, e.g., it is available under the trade name "mellojel" from the National Starch and Chemical company. In addition, in children under the age of two years, it is also preferred that the complex carbohydrate be administered together with the enzyme pancrease in an amount useful to promote digestion of complex carbohydrate. The pancrease is given adjunctively, usually in a dosage of about ¼ teaspoon of pancrease per 5 grams of complex carbohydrate.

Emulsifiers may be added for stability purposes to the diabetic supplement bar of the invention, e.g., emulsifiers such as lecithin.

Flavoring may also be added to the diabetic supplement bar of the invention to make it more palatable. Flavoring can be in a form of flavored extracts, volatile oils, chocolate flavoring, peanut butter flavoring, cookie crumbs, vanilla or any commercially available flavoring. For example, if flavoring which contains fat is used (e.g., chocolate flavoring contains butter fat), the fat concentration of the diabetic supplement bar of the invention should be adjusted accordingly so that the final fat concentration remains the same, i.e., the final fat concentration does not exceed 40% by weight fat.

Preservatives may also be added to the diabetic supplement bar of the invention to extend it's shelf time. Preferably, preservatives such as potassium sorbate, sodium sorbate, potassium benzoate, sodium benzoate or calcium disodium EDTA are used.

In addition to the carbohydrates, artificial sweeteners, e.g., saccharides, cyclamates, or aspartamine, may also be added to the diabetic supplement bar of the invention. Sorbitol should be avoided as a sweetener because sorbitol is not metabolized well by diabetic patients and in large quantities can cause diarrhea.

To prevent nighttime hypoglycemia during overnight sleep periods, the diabetic supplement bar of the invention is administered to the patient at bedtime. For example, the bar can be designed to provide 100 kcal of nutrition in the form of 1 bread exchange and ½ fat exchange. However, bars containing other exchange values depending upon the caloric value of the bar are embraced by this invention. Such exchange values are readily ascertained by the American Dietetic Association and the American Diabetes Association.

The bar of the invention provides a sufficient amount of circulating carbohydrates so that the patient passes the nocturnal sleep time without need for glucose intervention and awakens after about six to eight hours of sleep with a glucose level 60 mg/deciliter or greater. In addition, the diabetic supplement bar of the invention is dividable into smaller defined portions, e.g., four portions, so that each portion provides a controlled amount of calories. Any other possible partitions of the bar, e.g., where each portion may provide 10, 20, 25 or 50 kcal of nutrition, are also intended to be encompassed by this invention. Accordingly, the amount of the bar needed at bed time can be controlled depending on what the patient has eaten that day, e.g., the amount of food exchanges ingested before bedtime.

Certain terms used herein are described below for clarity.

As used herein the term "diabetic patient" refers to any patient who requires insulin injections to maintain blood glucose level as close as possible to a normal range, e.g., 80–120 mg/deciliter. For example, the patient suffers from diabetes, e.g., type I diabetes or type II diabetes and requires regular insulin administrations.

As used herein the term "hypoglycemia" refers to a clinical condition that results from low blood glucose levels, e.g., blood glucose levels of less than or equal to 3.0 mmol/liter or 60 mg/deciliter of whole blood. Symptoms of hypoglycemia fall into two main categories. Rapid epinephrine release can cause sweating, tremor, tachycardia, anxiety, and hunger. Central nervous system symptoms can include dizziness, headache, clouding of vision, blunted mental acuity, confusion, abnormal behavior, convulsions, and loss of consciousness.

EXAMPLE 1

This Example describes a diabetic supplement bar of the invention. The basic ingredients of the diabetic supplement bar (total weight 25 g) are set forth in Table 1.

TABLE 1

| Ingredient | Amount per 100 kcal (grams) | Total caloric contribution (kcal) | % of total caloric contribution |
|---|---|---|---|
| simple carbohydrate (sucrose) | 10 | 40 | 40 |
| protein (whey, casein or soy) | 3 | 12 | 12 |
| medium-chain triglycerides (coconut oil, palm oil and/ or palm kernel oil) | 1 | 8.3 | 8.3 |
| long-chain triglycerides (canola oil) | 2.1 | 18.9 | 18.9 |
| complex carbohydrate (uncooked corn starch) | 5 | 20 | 20 |

The possible additives to the diabetic supplement bar of the invention are set forth in Table 2.

TABLE 2

| | |
|---|---|
| ADDITIVES | |
| Ingredient | Amount per bar (total weight 25 g) |
| elemental Ca++ | 250 mg |
| vitamin C | 30 mg |
| lecithin | 0.5–2% |
| cookie crumb or vanilla | 0.5–2% |
| potassium sorbate | 500 mg |

1. Emulsifier: lecithin
2. Flavoring: flavoring can be in the form of a flavored extract, e.g., pure anise extract (73% ethanol), imitation banana extract (40% ethanol), imitation cherry extract (24% ethanol), chocolate extract (23% ethanol), pure lemon extract (84% ethanol), pure orange extract (80% ethanol), pure peppermint extract (89% ethanol), imitation pineapple extract (42% ethanol), imitation rum extract (35% ethanol), imitation strawberry extract (30% ethanol), or pure vanilla extract (35% ethanol); or volatile oils, e.g., balm oil, bay oil, bergamot oil, cedarwood oil, cherry oil, cinnamon oil, clove oil, origanum oil, or peppermint oil; peanut butter, chocolate flavoring, vanilla, cookie crumb, butterscotch or toffee in propylene glycol.

EXAMPLE 2

This example outlines one possible processing procedure for formulating the diabetic supplement bar of the invention.

This procedure can be carried out manually by a pharmacist or other trained personnel (kitchen help). The method of making the diabetic supplement bar of the invention can best be carried out by blending all of the ingredients in a blender and molding them into a bar. The total weight of the bar should not exceed 25 g including all the additives.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of controlling nighttime blood sugar levels in an insulin dependent diabetic patient comprising administering a diabetic supplement bar to the patient near bedtime, the diabetic supplement bar comprising about 10–60% by weight simple carbohydrate, about 1–25% by weight protein, about 2–40% by weight lipid and about 1–60% by weight complex carbohydrate.

2. The method of claim 1, wherein the diabetic patient requires insulin injections.

3. The method of claim 1, wherein the simple carbohydrate provides about 4–55 kcal per 100 kcal.

4. The method of claim 1, wherein the simple carbohydrate is selected from the group consisting of sucrose, glucose and dextrose.

5. The method of claim 1, wherein the protein provides about 10–20 kcal per 100 kcal.

6. The method of claim 1, wherein the protein is selected from the group consisting of whey, lactalbumin, casein, egg white, egg solids, soy and delactosed milk solid.

7. The method of claim 1, wherein the lipid provides about 10–40 kcal per 100 kcal.

8. The method of claim 1, wherein the lipid comprises a medium chain triglyceride and a long chain triglyceride.

9. The method of claim 8, wherein the medium chain triglyceride is selected from the group consisting of coconut oil, palm oil, palm kernel oil and mixtures thereof.

10. The method of claim 8, wherein the long chain triglyceride is selected from the group consisting of canola oil, safflower oil, sunflower oil, corn oil, olive oil, marine oil, peanut oil and mixtures thereof.

11. The method of claim 1, wherein the complex carbohydrate provides about 10–35 kcal per 100 kcal.

12. The method of claim 1, wherein the complex carbohydrate is selected from the group consisting of uncooked corn starch, nuts, barley, bulgur, pasta, parboiled rice, dried legumes and mixtures thereof.

13. The method of claim 1, wherein the bar further comprises sources of vitamins and minerals.

14. The method of claim 1, wherein the bar further comprises an emulsifier.

15. The method of claim 1, wherein the bar further comprises a flavoring.

16. The method of claim 1, wherein the lipid in an amount sufficient to delay gastric emptying in the patient.

17. A method for providing a continual source of glucose into the blood stream of an insulin dependent patient during nighttime, comprising administering to the patient near bedtime,
   (a) simple carbohydrate selected from the group consisting of sucrose, glucose and dextrose in an amount capable of being absorbed into the blood stream as glucose shortly after ingestion thereof;
   (b) protein in an amount sufficient to provide a source of glucose from gluconeogenesis after the simple carbohydrate has been cleared in the patient;
   (c) complex carbohydrate in an amount sufficient to provide a slow release of glucose from hydrolysis thereof; and
   (d) a lipid in an amount sufficient to delay gastric emptying in the patient.

18. The method of claim 17, wherein the diabetic patient requires insulin injections.

19. The method of claim 17, wherein the simple carbohydrate provides about 4–55 kcal per 100 kcal.

20. The method of claim 17, wherein the protein provides about 10–20 kcal per 100 kcal.

21. The method of claim 17, wherein the protein is selected from the group consisting of whey, lactalbumin, casein, egg white, egg solids, soy and delactosed milk solid.

22. The method of claim 17, wherein the lipid provides about 10–40 kcal per 100 kcal.

23. The method of claim 17, wherein the lipid comprises a medium chain triglyceride and a long chain triglyceride.

24. The method of claim 23, wherein the medium chain triglyceride is selected from the group consisting of coconut oil, palm oil, palm kernel oil and mixtures thereof.

25. The method of claim 23, wherein the long chain triglyceride is selected from the group consisting of canola oil, safflower oil, sunflower oil, corn oil, olive oil, marine oil, peanut oil and mixtures thereof.

26. The method of claim 17, wherein the complex carbohydrate provides about 10–35 kcal per 100 kcal.

27. The method of claim 17, wherein the complex carbohydrate is selected from the group consisting of uncooked corn starch, nuts, barley, bulgur, pasta, parboiled rice, dried legumes and mixtures thereof.

* * * * *